United States Patent [19]

Wu

[11] Patent Number: 5,385,530

[45] Date of Patent: Jan. 31, 1995

[54] ELECTRODE MASSAGING APPARATUS

[76] Inventor: Otto Wu, Room 918, 15 Fu Hsing N. Road, Taipei, Taiwan, Prov. of China

[21] Appl. No.: 139,721

[22] Filed: Oct. 22, 1993

[51] Int. Cl.[6] ............................................. A61N 1/32
[52] U.S. Cl. ........................................ 601/21; 601/15; 607/145; 607/115
[58] Field of Search ................. 601/15, 16, 17, 18, 601/19, 20, 21; 607/2, 39, 43–46, 75, 115, 145, 146, 150–151

[56] References Cited

U.S. PATENT DOCUMENTS

| 376,018 | 1/1888 | Whitney | 604/145 |
|---|---|---|---|
| 382,811 | 5/1888 | Horst | 601/15 |
| 1,454,528 | 9/1921 | Wiemann | 601/21 |
| 2,659,372 | 2/1950 | Andresen | 607/151 |
| 2,994,324 | 3/1959 | Lemos | 607/151 |
| 5,203,349 | 4/1993 | Kogan | 607/145 |

FOREIGN PATENT DOCUMENTS 975013  11/1982  U.S.S.R. ................................ 601/21

Primary Examiner—Max Hindenberg
Assistant Examiner—David J. Kenealy
Attorney, Agent, or Firm—Morton J. Rosenberg; David I. Klein

[57] ABSTRACT

A massaging apparatus employing a voltage producing device is provided. The voltage producing device produces an instantaneous impulse voltage for passing a current to the veins, arteries and vital points of a human body to stimulate the function of the internal organs.

1 Claim, 3 Drawing Sheets

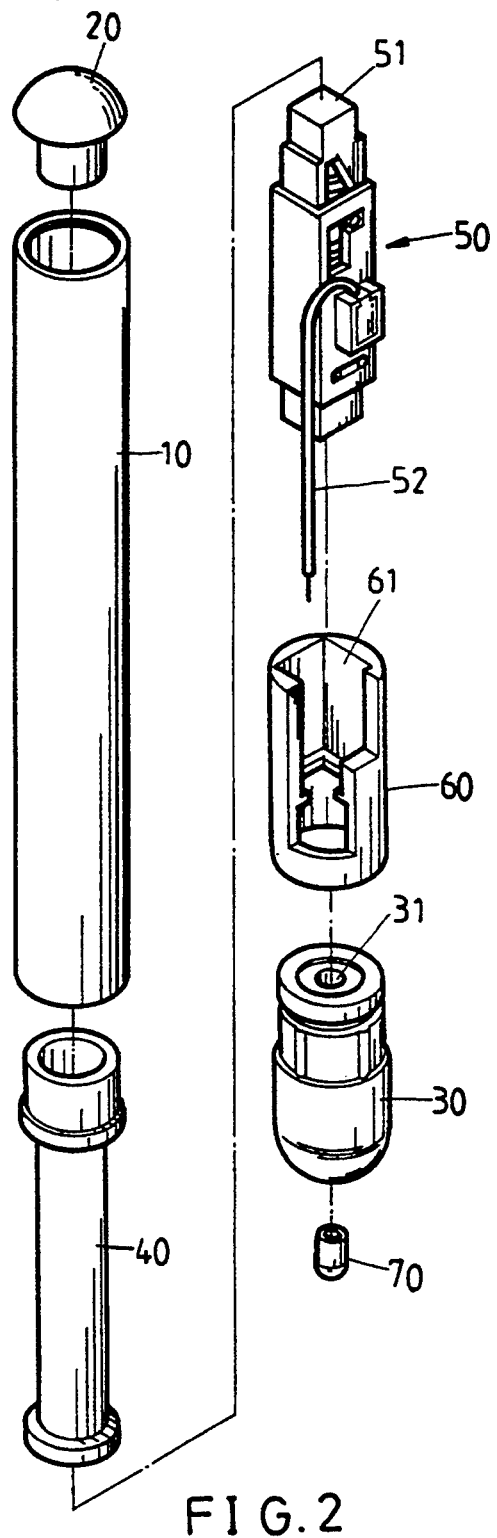
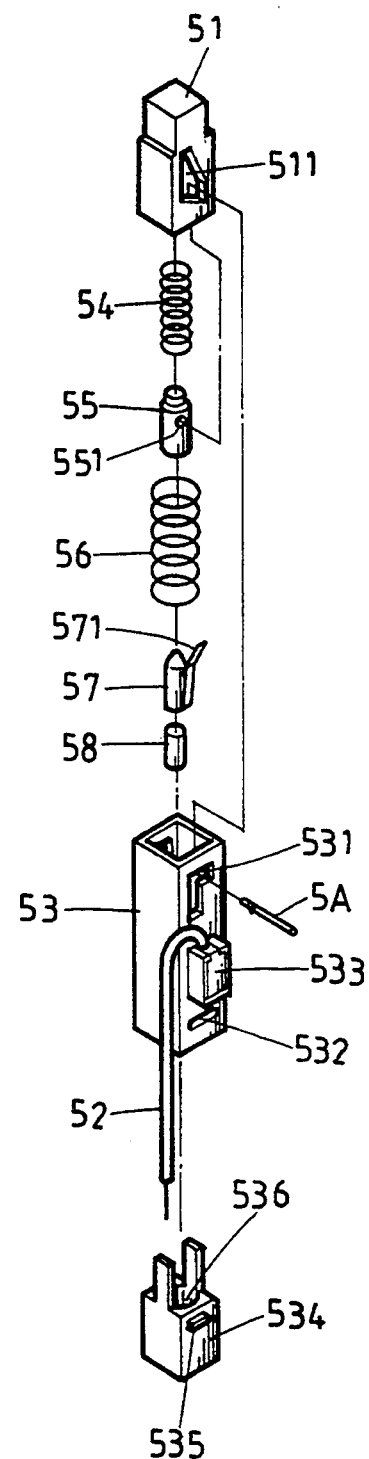
FIG. 2
FIG. 3

ELECTRODE MASSAGING APPARATUS

BACKGROUND OF THE INVENTION

The present invention relates to a massaging apparatus, in particular, to a massaging rod being applied onto the arteries, veins and vital points of the human body so as to stimulate the internal organs of the body.

At present, there are numerous types of ailments which arise from prolonged hours of working. For instance, partial muscle cramps, and other types of muscle ailments are commonly found in office workers who work for prolonged period. As a result, massaging apparatuses have been developed to stimulate the relaxation of the veins and arteries. In the prior art, massaging apparatuses are of the pressing type or the electric powered type. In the pressing type, the user makes use of the massaging device to press with great force on the muscle so as to stimulate the veins and arteries, and vital points of the muscle. However, the pressing type massaging apparatus has to be driven by the user and therefore, it is not convenient to use.

In the electric-powered type of massaging apparatus, electric current from either a battery or transformer is employed to drive a motor of the vibration apparatus of the massaging apparatus. By constant vibrating at the positions of veins, arteries and vital points on the human body, treatment to the muscle can be obtained. The power supply of the massaging apparatus has to be maintained, and thus, the range of the application of the electric powered massaging apparatus is limited. That is, it is not convenient to be taken on trips, and the parts of the motor and the vibration means are easily damaged.

SUMMARY OF THE INVENTION

A primary object of the present invention is to provide a massaging apparatus which has a simple structure and is portable.

Another object of the present invention is to provide a massaging apparatus which employs a voltage-producing means to produce a high voltage impulse current.

It is another object of the present invention to provide a massaging apparatus which produces an instantaneous impulse current which is transferred to the locations of the arteries, veins and vital points of the human body.

BRIEF DESCRIPTION OF THE DRAWINGS

FIG. 2 is an exploded view of the massaging apparatus in accordance with the present invention;

FIG. 3 is an exploded view of the voltage-producing means in accordance with the present invention;

DETAILED DESCRIPTION OF THE PREFERRED EMBODIMENT

Figure 1:
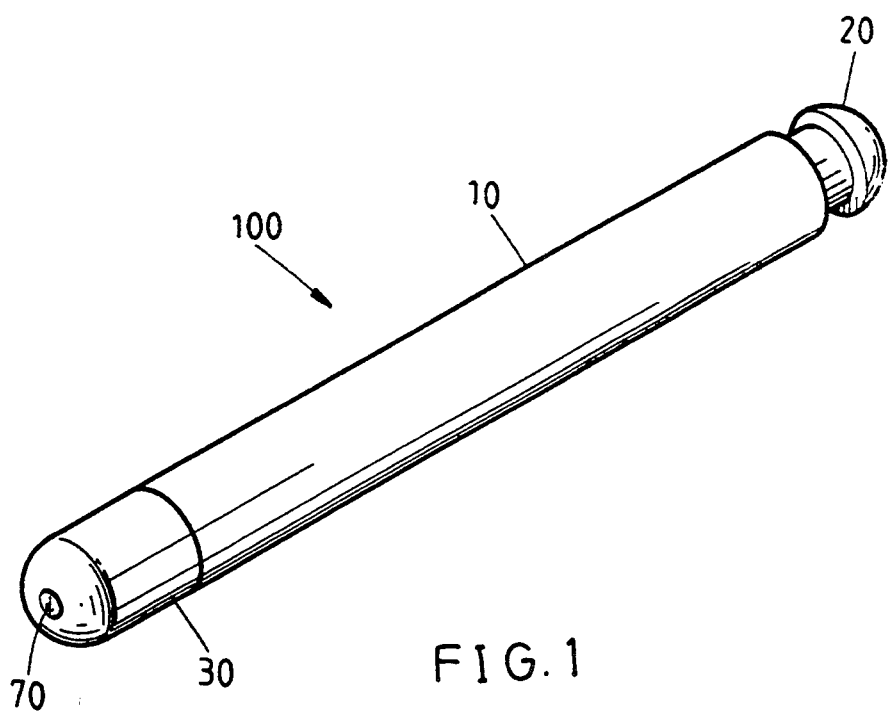
FIG. 1 is a perspective view of the massaging apparatus in accordance with the present invention.

Referring to FIGS. 1 and 2, there is shown, the massage rod 100 comprising a housing 10, a button 20 and an electrode cover 30. The housing 10 has a substantially elongated shape with the button 20 and the electrode cover 30 respectively mounted on opposing ends of the housing 10. The lower end of the button 20 is engaged with one end of a movement controlling rod 40. The opposing or lower end of the rod 40 is mounted with a voltage producing means 50. In accordance with the present invention, the voltage producing means 50 produces a voltage by means of pressing two different semiconductors together with an impact force.

At the top of the voltage-producing means 50 there is provided a pressing section 51, the pressing section 51 being in contact with the lower end of the movement controlling rod 40. On one lateral face of the voltage producing means 50 an output lead 52 is extended therefrom. The output lead 52 transfers the instantaneous high voltage impulse from the voltage producing means. An insulative cover 60 has an internal cavity for receipt of the voltage producing means 50 therein, and insulating the voltage producing means from the housing 10. The lower portion of the insulative cover 60 is engaged with the electrode cover 30.

The center region of the electrode cover 30 is provided with a hole 31 through which the output lead 52 of the voltage producing means 50 passes. The end of the electrode cover 30 is mounted with an electrode element 70. The electrode element 70 is formed from a material having conductivity and is electrically connected to the output lead 52 of the voltage producing means 50 so as to conduct the instantaneous voltage impulse from output lead 52 to the user's body portion in contact therewith.

As shown in FIG. 3, a step-like hole 511 is formed through the two lateral faces of the pressing portion 51. An external cover member 53 is provided having two L-shaped slots 531 formed through opposing sides thereof, and located in correspondence to the steplike holes 511. At each of the two lateral faces of the lower end of the external cover member 53 there is formed a fastening slot 532. On one of the lateral faces of the external cover member 53 an insulative section 533 is provided for extension of the output lead 52 therefrom. Each of the lateral ends of the base seat 534 is provided with a protruding rail 535 disposed in correspondence with a respective fastening slot 532 for coupling of the base seat 534 to the end of the external cover member 53. At the center region of the upper end of the base seat 534, an accommodation recess 536 is provided.

The structure of a voltage-producing means 50 is shown in FIG. 3, wherein, between the pressing section 51 and the base seat 535, a spring 54, an impact block 55, a movement controlling spring 56, a first metallic block 57, and a second metallic block 58 are mounted in sequence. The second metallic block 58 is adapted to be received within the accommodation recess 536 of the base seat 534. The lateral face of the impact block 55 is provided with a hole 551 formed therethrough and disposed in correspondence with the steplike holes 511 of the pressing portion 51 and the long L-shaped slots 531. A pin 5A is inserted through the L-shaped slots 531, step-like holes 511 and hole 551, such that the impact block 55 and the pressing section 51 are mounted to the top end of the external cover member 53. The first metallic block 57 and the second metallic block 58 are respectively formed of different material compositions. A conductive plate 571 is mounted to the bottom end of the first metallic block 57, and the conductive plate 571 is connected to the output lead 52.

Figure 4:
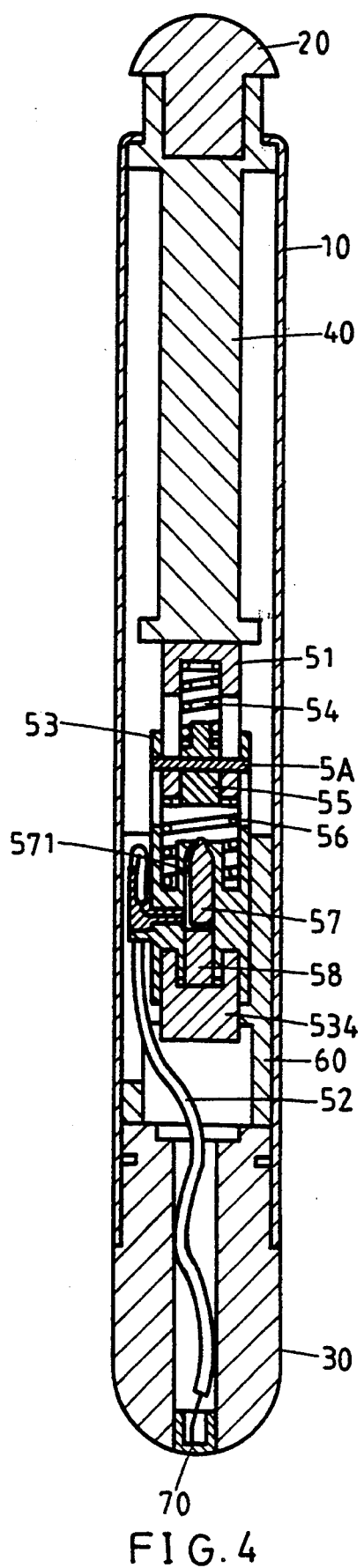
FIG. 4 is a cross-sectional elevational view of the present invention.

Referring to FIG. 4, the assembled device is shown before the button 20 is pressed for operation. The movement controlling rod 40 is in contact with the top end of the pressing section 51 of the voltage producing means 50. At this time, the movement controlling spring 56 is in an uncompressed state, and a gap is maintained between the impact block 55 and the first metallic block 57. There is no impact between the first metallic block 57 and second metallic block 58. Thus, there is no instantaneous high voltage impulse produced at the conductive plate 571 and there is no output at the output lead 52 of the voltage-producing means 50. Thus, there is no current produced from the electrode 70.

Figure 5:
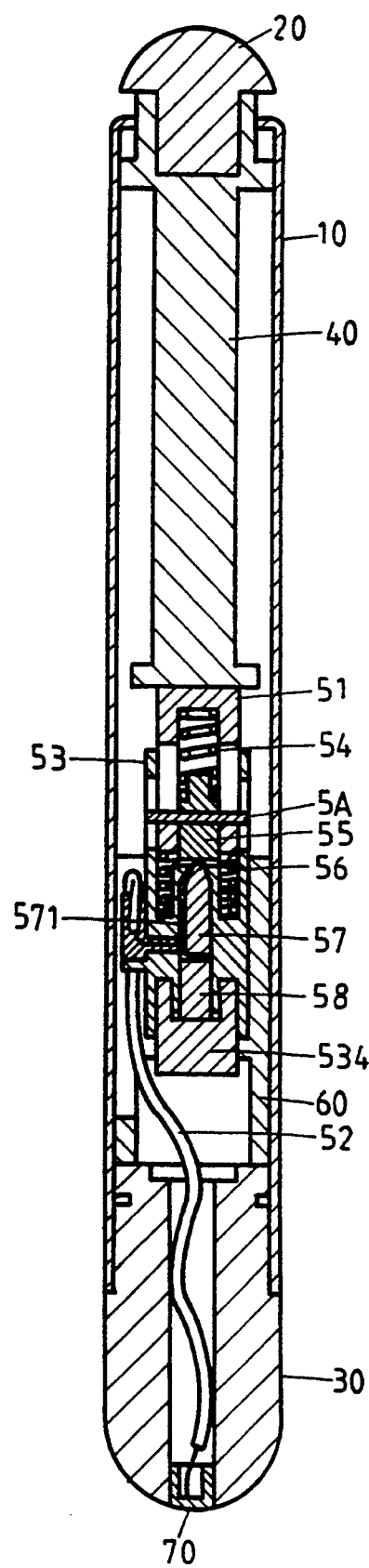
FIG. 5 is a cross-sectional view showing the action of the voltage-producing means.

When the button 20 is pressed, as shown in FIG. 5, the pressing force urges the movement controlling rod 40 to press down the pressing section 51 of the voltage producing means 50. That displacement causes the spring 56 to be compressed. At the same time, the impact block 55 urges the first metallic block 57 to transfer the pressure to the metallic block 58. Due to the fact that the second metallic block 58 is mounted to the base seat 534, the respective faces of the first metallic block 57 and the second metallic block 58 which contact each other produce an impact force. As a result of the differences in material composition of the first metallic block 57 and the second metallic block 58, the energy of the impact is transformed to electric energy. Thus, an instantaneous impulse voltage is produced at the conductive plate 571 and then transferred from the output lead 52. The voltage is conducted to the electrode element 70 through the insulative cover 60 by lead 52. The electrode element 70 outputs the instantaneous voltage impulse to the user's body, the user applying the electrode element 70 so as to make contact with the veins, arteries and vital points of the body. This conduction of current from the instantaneous high voltage impulse stimulates the veins, arteries and vital points of the human body and strengthens the function of the internal organs of the human body.

I claim:

1. A massaging apparatus having a rod-like contour, comprising:
   a. a longitudinally extended housing, said housing having a bore extending longitudinally therethrough between opposing open ends thereof;
   b. an electrode cover mounted in a first of said opposing open ends of said housing, said electrode cover having an opening formed longitudinally therethrough;
   c. a conductive electrode member disposed at a distal end of said electrode cover within said opening formed in said electrode cover;
   d. an insulative cover member disposed within said housing adjacent said electrode cover, said insulative cover member having a through bore formed longitudinally therethrough;
   e. a button member displaceably mounted in a second of said opposing open ends of said housing;
   f. a movement controlling rod member disposed within said housing and having a first end thereof coupled to said button member; and,
   g. voltage generating means disposed within said through bore of said insulative cover and having one end thereof coupled to a second end of said movement controlling rod member for generating an impulse voltage responsive to displacement of said button member, said voltage generating means including (1) a cover member disposed within said insulative cover and having a bore extending longitudinally therethrough, (2) a base seat member secured to a distal end of said cover member and forming a closure for a respective end of said bore of said cover member, (3) a pressing member displaceably mounted at a proximal end of said cover member and biased by a first spring member, (4) an impact block member coupled to said pressing member and biased by a second spring member, (5) a first metallic block member disposed within said bore of said cover member between said impact block member and said base seat member, said first block member having a conductive plate extending therefrom, (6) a second metallic block member disposed within said bore of said cover member between said first metallic block member and said base seat member, said first block member being formed of a material composition different from that of said second block member for generating an impulse voltage responsive to an impact force being applied by said impact block member to said first and second metallic members, said impact force being generated responsive to displacement of said button member by a user, and (7) a conductive lead member having one end coupled to said conductive plate of said first metallic block member and an opposing end coupled to said conductive electrode member for coupling said impulse voltage therebetween.

* * * * *